United States Patent [19]

Takeda et al.

[11] 4,263,457

[45] Apr. 21, 1981

[54] PROCESS FOR PRODUCING BIPHENYL DERIVATIVES

[75] Inventors: Makoto Takeda; Eiji Taniyama; Yuji Ozawa; Makoto Imanari; Kunimasa Takahashi; Hiroshi Iwane, all of Ami, Japan

[73] Assignee: Mitsubishi Petrochemical Company, Ltd., Tokyo, Japan

[21] Appl. No.: 67,550

[22] Filed: Aug. 17, 1979

[30] Foreign Application Priority Data

Aug. 18, 1978 [JP] Japan .................................. 53/100771

[51] Int. Cl.³ ........................ C07C 45/65; C07C 29/00
[52] U.S. Cl. ................................ 568/316; 260/465 G; 560/102; 562/492; 568/807; 585/430; 585/431; 570/129; 570/184
[58] Field of Search ............... 260/592, 590 D, 650 A, 260/650 R, 465 G, 649 F, 649 DP; 585/430, 431; 560/102; 568/316, 809; 562/491, 492

[56] References Cited

U.S. PATENT DOCUMENTS

| | | | |
|---|---|---|---|
| 2,182,431 | 12/1939 | Groll et al. | 260/650 A |
| 2,184,235 | 12/1939 | Groll et al. | 260/650 A |
| 2,932,673 | 4/1960 | Melik et al. | 585/430 |
| 3,228,992 | 1/1966 | Myers | 585/430 |
| 3,452,079 | 6/1969 | Shen et al. | 260/649 DP |
| 3,583,903 | 6/1971 | Miale et al. | 585/430 |
| 3,714,281 | 1/1973 | Hayes et al. | 585/430 |
| 3,928,481 | 12/1975 | Suggitt | 585/430 |

OTHER PUBLICATIONS

Fieser et al., "Reagents for Organic Synthesis", pp. 1118-1119 (1965).

Primary Examiner—James H. Reamer

Attorney, Agent, or Firm—Robert E. Burns; Emmanuel J. Lobato; Bruce L. Adams

[57] ABSTRACT

A process for producing a halobiphenyl derivative represented by the following formula (I) comprises dehydrogenating a cyclohexylhalobenzene represented by the following formula (II) under such conditions that substantially no dehalogenation occurs.

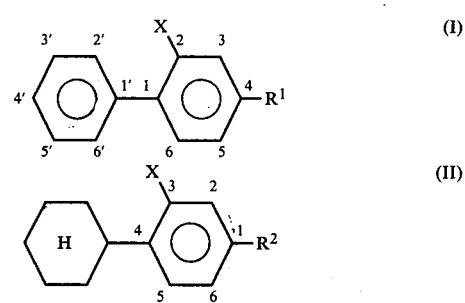

wherein X represents a halogen atom, and each of $R^1$ and $R^2$ independently represents a group represented by the formula

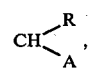

wherein A represents carboxyl or an alkoxycarbonyl group and R represents a hydrogen atom or a lower alkyl group; an alkylcarbonyl; alkenyl; alkynyl; alkyl; aryl; arylcarbonyl; hydroxyalkyl; cyanoalkyl or cyanoalkenyl group.

8 Claims, 1 Drawing Figure

PROCESS FOR PRODUCING BIPHENYL DERIVATIVES

BACKGROUND OF THE INVENTION

1. Field of Art

The present invention relates to a process for producing biphenyl derivatives. More particularly, the present invention relates to a process for producing biphenyl deviatives which is characterized in that a biphenyl skeleton is formed by the dehydrogenation of a cyclohexylbenzene structure.

More specifically, the present invention relates, in one embodiment thereof to a process for producing 4-biphenylylacetic acid derivatives or intermediates thereof which are useful, for example, as anti-inflammatory, analgesic and antipyretic agents.

2. Prior Art

Generally, the introduction of a substituent into a specific position of a biphenyl derivative or the synthesis of a biphenyl derivative having a substituent at a specific position is often difficult depending upon the position into which the substituent is introduced.

For example, with regard to the synthesis of a biphenyl skeleton of 4-biphenylylacetic acids including α-methyl-(2-fluoro-4-biphenylyl)acetic acid which is a particularly well-known anti-inflammatory agent among the above mentioned 4-biphenylylacetic acid derivatives, Japanese Patent Publication No. 28369/1970 discloses, as a process for synthesizing biphenyl derivatives whose intermediates have a predetermined position for a substituent, an Ullmann's condensation process wherein a bromobenzene derivative is reacted with an equimolar or more of iodobenzene and metallic copper and a diazophenylation process wherein an aniline derivative is subjected to diazotization, and the resulting diazo compound is reacted with benzene.

However, the former process is accompanied by a problem in that iodobenzene, which is expensive, is used in an excessive amount and iodobenzene or the starting material is inevitably condensed with each other due to the cross condensation reaction. On the other hand, the latter process involving the diazotization is accompanied by a problem in that the synthesis of the starting aniline derivative is difficult depending upon the position of the substituent of the intended compound. Further, it cannot but the said that the yield of the diazophenylation reaction is low.

SUMMARY OF THE INVENTION

The present invention aims at overcoming the above mentioned problems and contemplates achieving this object by forming a biphenyl skeleton through the dehydrogenation of a cyclohexylbenzene structure.

Accordingly, the process for producing a halobiphenyl derivative represented by the following formula (I), according to the present invention, is characterized by dehydrogenating a cyclohexylhalobenzene derivative having the following formula (II) under such conditions that no substantial dehalogenation occurs.

wherein: X represents a halogen atom; and $R^1$ and $R^2$ independently represent a group represented by the formula an alkylcarbonyl, alkenyl, alkynyl, alkyl, aryl, arylcarbonyl, hydroxyalkyl, cyanoalkyl or cyanoalkenyl group, A representing a carboxyl or alkoxycarbonyl group and R representing hydrogen atom or a lower alkyl group.

If the substituent $R^2$ of a starting cyclohexylbenzene derivative (formula (II)) undergoes no change due to the dehydrogenation reaction, the substituent $R^2$ is the same as the substituent $R^1$ of the resulting biphenyl derivative (formula (I)).

One of the important features and advantages of the present invention is thus that a biphenyl skeleton of 4-substituted biphenyl (formula (I)) which is substituted by a halogen atom at its 2-position is formed not by a process for condensating aromatic hydrocarbons with each other, which is difficult to carry out, but by a process for dehydrogenating cyclohexylbenzene (formula (II)) in the same substitution state, which is easy and inexpensive to carry out industrially.

The dehydrogenation is carried out "under such conditions that no substantial dehalogenation occurs" which will be discussed in detail hereinafter. Accordingly, the dehydrogenation of a starting cyclohexylhalobenzene derivative (formula (II)) gives the corresponding halobiphenyl derivative and, as a result, no further halogenation process is necessary.

Another advantage of the present invention is that a cyclohexylhalobenzene derivative, which is a starting material, is easy to synthesize, which will be described in detail hereinafter. Particularly, when the X of the formula (I) or (II) represents a halogen, this feature is remarkable. For example, cyclohexylbenzene constituting a basic structure can be easily synthesized by the Friedel-Crafts reaction of benzene and cyclohexene. A substituent ($R^2$) in the 1-position, when it represents, for example, an alkylcarbonyl group, can be easily introduced by the Friedel-Crafts reaction of a carboxylic acid halide or carboxylic acid anhydride corresponding to the cyclohexylbenzene. Other substituent ($R^2$) in the 1-position may also be easily introduced directly or from the alkylcarbonyl group. Also, the 2-position substituent may be selectively introduced into the 2-position when the 4-position substituent already introduced is meta-orientating.

As is apparent from the definition of the substituent $R^1$ of the compound represented by the formula (I), the compounds belonging to the formula (I) are all 4-biphenylylacetic acids which are useful as anti-inflammatory, analgesic and antipyretic agents or those compounds which are capable of being converted into 4-biphenylylacetic acid by a conventional process as described in detail hereinafter. For example, in the case where the substituent $R^1$ represents and A represents a carboxyl group, the compound (I) is a 4-biphenylylacetic acid (additionally, in the case where R is a methyl group and X is fluorine, the compound is the above mentioned preferred anti-inflammatory agent). Furthermore, in the case where $R^1$ represents a group other than conversion of the group into a carboxyl group can be easily carried out according to knowledge of organic synthesis provided that they are selected from the above specified group.

BRIEF DESCRIPTION OF THE DRAWING

In the accompanying drawing, the single FIGURE is a chart showing various reaction schemes for obtaining the biphenylylacetic acid derivatives from cyclohexene and benzene.

DETAILED DESCRIPTION OF THE INVENTION

1. Starting cyclohexylhalobenzene derivative and resultant halobiphenyl derivative These compounds are represented by the formulae (I) and (II). As a halogen represented by X, fluorine, chlorine, bromine and iodine are suitable. From the viewpoint of medical effects as a 4-biphenylylacetic acid derivative, fluorine is particularly suitable.

$R^1$ and $R^2$ represent the above given respective definitions. In these definitions, the "alkyl", "alkenyl", "alkynyl" (including the hydroxy and cyano derivatives thereof) and "alkoxy" groups have usually from about 1 to 4 carbon atoms.

The lower alkyl group of R usually has from about 1 to 3 carbon atoms.

The most preferable compound among the 4-biphenylylacetic acid derivatives is one wherein $R^1$ represents (particularly where R is methyl). In the case where a starting cyclohexylhalobenzene derivative (II) does not have this group, the $R^2$ group of the compound (II) is typically exemplified by lower alkylcarbonyls such as acetyl; ethyl; and —CH(OH)CH$_3$. When $R^2$ represents ethyl, the ethyl group is also dehydrogenated in the dehydrogenation reaction to form the compound (I) where the substituent $R^1$ is ethenyl, and similarly, when $R^2$ represents —CH(OH)CH$_3$, the —CH(OH)CH$_3$ is also dehydrogenated in the dehydrogenation reaction to acetyl.

2. Dehydrogenation reaction

As described above, the present invention provides a process for producing a halobiphenyl derivative of the formula (I) through the dehydrogenation of a cyclohexylhalobenzene derivative of the formula (II).

The dehydrogenation reaction of the present invention can be carried out by any process usable for dehydrogenation/aromatization of a cyclohexane ring in consideration of the presence of the substituents $R^1$ and X in the compound (II). In accordance with the present invention, the dehydrogenation reaction is carried out under such conditions that no substantial dehalogenation occurs. Such dehydrogenation can be realized by the choice of the dehydrogenating agent to be used in the case of chemical dehydrogenation, and it can be realized by the choice of the catalyst to be used in the case of catalytic dehydrogenation.

(1) Chemical dehydrogenation

As a dehydrogenating agent causing no substantial dehalogenation, sulfur is suitable. Sulfur is preferably in the form of a powder.

In the case where the dehydrogenation is carried out by the use of sulfur, it is preferable that sulfur be used in a quantity which is 3 times by mole (theoretical quantity) to 6 times by mole (2 times the theoretical quantity) the quantity of the reactant. In some case, the sulfur may be added in a divided manner. A solvent or dispersion medium may or not be used. When used, solvents or dispersion mediums which are stable under the reaction conditions, such as diphenyl ether and α-chloronaphthalene, are suitable. The dehydrogenation reaction is carried out at a temperature of from about 200° to 350° C., preferably from 230° to 280° C.

The dehydrogenation reaction is carried out by subjecting a starting cyclohexylhalobenzene derivative and sulfur to the above conditions under stirring until the desired level of conversion is attained, for example, for a period of no less than several hours.

(2) Catalytic dehydrogenation (1) Type of preferable catalyst

As a catalyst causing substantially no dehalogenation, a catalyst comprising a catalytic active component of a metal oxide, which is selected from the group consisting of tungsten oxides, zirconium oxides and mixtures of tungsten oxides and zirconium oxides, supported on a refractory inorganic compound is suitable.

A number of processes have been heretofore studied to catalytically dehydrogenate alkyl-substituted benzenes into alkenylbenzenes. On the basis of these studies, it is easily estimated that when an alkyl group is a cyclohexyl group, a biphenyl compound is synthesized. However, when a potassium-promoted iron oxide catalyst such as "Shell 105", which is famous as a catalyst for the dehydrogenation of alkylbenzenes of this type, particularly ethylbenzene, and a platinum-based catalyst useful for the dehydrogenation and dehydrocyclization reaction of n-paraffins are used, a dehalogenation reaction, in addition to the dehydrogenation reaction, occurs in the case of alkyl benzenes having a halogen atom in their nucleus, and the intended products, therefore, cannot be obtained in a high yield.

(2) Definition of preferable catalyst

(i) Catalytically active component

The terms "tungsten oxides" and "zirconium oxides" as used herein are intended to include, in addition to oxides of tungusten and oxides a zirconium alone, respectively, co-oxides of tungsten and/or zirconium and co-oxides or binary or ternary oxides of tungsten and/or zirconium and a metal capable of forming such oxides as aluminum, titanium, iron and cerium. Ordinarily, the content of metals other than tungusten and zirconium does not exceed the content of tungsten and zirconium. However, when metals other than tungsten and zirconium also constitute the component of a support, the content of the metals is ordinarily greater than the content of tungsten and zirconium.

The term "mixture of tungsten oxides and zirconium oxides" as used herein is intended to include, in addition to mixtures of the respective metal oxides (these oxides can be co-oxides with other metals as described above), co-oxides of tungsten and zirconium and optionally other metals.

(ii) Support

The preferable catalytically active component is used in the form of a supported catalyst. The term "support" as used herein, which may alternatively be called "carrier", is intended to include, in addition to those which merely support physically the above mentioned catalytically active component or serve to spread the surface area of the catalytically active component thereby to enhance the contact efficiency of the active component, those which contribute to the dehydrogenation reaction to a favorable degree, singly or in cooperation with tungsten and/or zirconium.

Depending upon the process for producing the supported catalyst, tungsten or zirconium and the metal of the metal oxides of the suppport may form a co-oxide. In such a case, it is probable that the catalytic activity is attributable to the co-oxide. Such a contribution of a support to the dehydrogenation reaction is evident from the fact that some types of supports do not always afford a high selectivity in the dehydrogenation reaction, or, when titania and tungsten oxides are independently used, respectively, a high selectivity in the dehydrogenation reaction is not obtained, but when these compounds are used in combination with each other, a remarkably high selectivity in the dehydrogenation reaction is obtained.

It is preferable that the dehydrogenation reaction using the preferable catalyst be carried out at a relatively high temperature, for example, from 400° to 700° C. Accordingly, a material for the support should be one which is stable under such temperatures, i.e., a refractory inorganic compound.

It is preferable that such a refractory inorganic compound be an oxide (including a co-oxide) containing, as a main component, at least one member selected from the group consisting of titanium, zirconium, aluminum, iron, calcium, magnesium, cerium and tin. Among these oxides, particularly preferable is a metal oxide whose metal is selected from the group consisting of titanium, zirconium, aluminum, iron and cerium. Zirconium oxides are classified as being both a catalytically active component and a support herein, and a catalyst consisting entirely of a zirconium oxide also falls under the category of a supported catalyst as a catalyst comprising a catalytically active component consisting essentially of a zirconium oxide which is supported on a support of a zirconium oxide.

Furthermore, as a refractory inorganic compound, in addition to the above mentioned preferable oxides, use may be made of any known catalyst supports, such as an oxide of a member selected from the group consisting of silicon, zinc, cadmium, strontium, barium, vanadium, niobium, tantalum, chromium, molybdenum, uranium, cobalt, nickel, copper, potassium, indium, germanium, lead, antimony and a mixture of rare earth metals.

Because of its use at a relatively high temperature, a refractory inorganic compound usually is an oxide. However, sulfates and phosphates of these metals may also be used as far as circumstances permit.

Although it is desirable that the support contain the above mentioned elements as a main component, it may also contain other components in a small quantity of from 0 to 10% by weight. For example, alkali metals, selenium, tellurium and thallium may be added provided that they do not occupy the major proportion of the support. Potassium is one of the components which result in favorable effects when added in a small quantity.

Examples of the support are alumina, silica-alumina, titania, zirconia, titania-zirconia and magnesia.

(3) Materials for preparing catalyst

The material from which the catalyst of the present invention is prepared may be any material which is available for industrial purposes and is capable of being converted into an oxide on firing. Preferring examples of the material for the tungsten source are ammonium paratungstate, silicotungstic acid, tungsten oxides and ammonium tungstate. Preferred examples of the material for the zirconium source are zirconium oxychloride, zirconyl hydroxide, zirconyl sulfate, zirconyl carbonate, zirconyl nitrate, zirconium tetrachloride, zirconyl stearate and zirconium oxides. These materials may be used as such or in the form of a hydrogel derived therefrom by neutralization with aqueous ammonia.

(4) Materials for support

The material from which the support is prepared depends upon the material used as the support. Generally, any material which is useful as a raw material for the support may be used. Examples of such a material are sulfates, nitrates, halides, hydroxides and oxides of the metal element of the support. Preferred examples of the material for preparing the particularly preferable supports as described above are titanium tetrachloride, titanyl sulfate and metatitanic acid for titania; materials for preparing zirconia are those described in terms of the material for preparing the catalyst active. Examples of the material for preparing iron oxides are ferric chloride, ferric sulfate, iron nitrates, iron powder, iron scrap, iron hydroxides and iron oxides; preferred examples of the material for preparing alumina are alumina, aluminum sulfate and aluminum chloride; and examples of the material for the cerium source are ammonium cerous nitrate, ammonium ceric nitrate, cerous nitrate, cerium carbonates, ceric hydroxide, cerous chloride, cerium acetates, cerous oxalate, cerous sulfate, ceric sulfate and ceric oxide.

(5) Preparation of catalyst

The catalyst which is used in the present invention may ordinarily be prepared by any process for producing multi-metal oxide catalysts of this type.

More specifically, use may be made of a process wherein aqueous ammonia is added to an aqueous mixed solution of soluble salts of the metals of the catalyst and support components to co-precipitate the corresponding metal hydroxides or a process wherein the hydroxides of the metals of the catalyst and support components are separately precipitated, and the resulting respective hydroxides are kneaded together.

In the case where tungsten is used as a catalyst component, an aqueous solution or an aqueous ethanolamine-containing solution of ammonium paratungstate or ammonium paratungstate powder is thoroughly mixed with a support component such as a hydroxide or oxide of a member selected from the group consisting of titanium, zirconium, iron, cerium and aluminum. In the case where zirconium is used as a catalyst component, use may be made of a process for co-precipitating zirconium hydroxide and a metal hydroxide of the support component to be used, a process comprising mixing zirconium hydroxide and a metal hydroxide of the support component to be used together, or a process comprising mixing a zirconium salt such as zirconyl nitrate with a hydroxide or oxide of the support component as described above.

The mixture thus obtained is formed into a suitable shape, which is thereafter fired or calcined at a temperature of from about 500° to 1000° C. For the sake of convenience of shaping, the mixture can be fired before shaping and then used. The mixture may be shaped by any conventional forming methods such as extrusion, tabletting and tumbling pelletizing process.

In addition, the catalyst of the present invention may also be prepared by methods other than the above described mixing processes, such as a so-called impregnating or coating process. For example, a preformed support of such as alumina, silicaalumina, titania, zirconia, ceria or iron oxide may be impregnated with a soluble salt of tungsten, zirconium or both or coated with a salt, hydroxide or oxide of tungsten, zirconium or both and thereafter, fired.

The catalyst may be of any shape such as cylindrical, spherical, honeycomb and macaroni shape, as desired.

The content of the catalytically active component (an oxide of tungsten and/or zirconium) in the final catalyst is in the range of from about 1 to 70 mole %, preferably from about 2 to 50 mole %, and more preferably about 2 to 20 mole %.

(6) Catalytic dehydrogenation reaction

The reaction using the catalyst prepared above will be described in detail below.

(i) Reaction material

The material which is used in the present reaction is one which is represented by the formula (II). It is preferable that a solvent for the material and a diluent be used. Any solvent which does not interfere with the reaction and the purification of the final product may be used as a solvent for the material. Benzene and toluene are suitable. A preferred diluent is water and nitrogen.

(ii) Reaction condition

In the reaction of the present invention, any reactor which is usually used in a gas phase reaction, such as multi-tubular heat exchanger type, radial flow type or adiabatic type reactor, may be used. The reaction may be carried out in a fixed bed, moving bed or fluidized bed. The reaction is carried out at a temperature of from about 400° to 700° C., preferably from 500° to 650° C. The reaction temperature outside the above mentioned range may also be used. However, at a temperature outside a temperature range of from 300° to 800° C., the reaction may not be easily carried out economically. The reaction may be carried out at a pressure equal to, below, or above atmospheric pressure. However, the reaction is facilitated when carried out at a pressure near atmospheric pressure. The reactant is supplied at a gas space velocity of the order of from 50 to 10,000 per hour as calculated in terms of an empty column basis of a reactor, a temperature of 0° C. and a pressure of 1 atmosphere.

(iii) Reaction product

For example, when water and a solution of the starting material in benzene are supplied into a reactor packed with the catalyst, the dehydrogenation product, water, the starting material, by-products and the solvent are discharged from the reactor. The dehydrogenation product can be easily recovered by distillation. In the case where the substituent $R^2$ of the starting material represents an alkyl group, this $R^2$ portion can also be dehydrogenated. Also, when the substituent $R^1$ represents a hydroxyalkyl group, this moiety may also be dehydrogenated to a carbonyl group.

3. Analysis of the present invention as technology for preparation of 4-biphenylylacetic acids (1) Conversion within the compound (I)

As described hereinbefore, the compounds (I) are all 4-biphenylylacetic acids or precursors or intermediates thereof (it being understood that these precursors or intermediates may be utilized by themselves or converted into other compounds) which are useful as anti-inflammatory, analgesic and antipyretic agents.

Although the $R^1$ group represents the substituents as defined above, these substituents may be interchanged with each other. Accordingly, in the case where the substituent $R^2$ in the compound (formula (II)) before being subjected to dehydrogenation is different from the substituent $R^1$ in the final compound (formula (I)), for example, when the compound (formula (II)) to be dehydrogenated is synthesized, supposing that a compound (I) has a substituent $R^2$ other than a desired substituent $R^1$, the substituent $R^2$ may be converted into the desired substituent after the dehydrogenation. More specifically, in the case where $R^1$ represents a group and A represents a carboxyl group in the formula (I), this compound is a 4-biphenylylacetic acid. However, when A represents an alkoxycarbonyl group, the non-acetic acid compound may be converted to a 4-biphenylylacetic acid, for example, by a hydrolysis process described in Japanese Pat. No. 28369/70 or Japanese Pat. Laid-Open No. 55543/1979 directed to a prior invention by the present inventors.

In the case where $R^1$ represents hydroxyethyl, conversion of the compound (I) into a desired 4-biphenylylacetic acid derivatives may be made by a known method shown in Japanese Pat. Laid-Open No. 76233/1976.

In the case where $R^1$ represents a hydroxyalkyl, conversion of the compound (I) into an α-methyl-4-biphenylylacetic acid, a compound falling within the desired 4-biphenylylacetic acids, may be made by a known method shown in Japanese Pat. Laid-Open No. 18533/1978.

In the case where $R^1$ represents an alkylcarbonyl group, the compound (I) may be converted to the desired 4-biphenylylacetic acid derivatives by various methods described in Japanese Pat. Nos. 28369/73 and 18105/72, and Japanese Patent Application Laid-Open No. 153932/77.

In the case where $R^1$ represents an alkenyl group, for example, a vinyl group, the compound (I) may be converted into an α-methyl-4-biphenylylacetic acid which is one type of the intended 4-biphenylylacetic acids by a method described in Japanese Patent Application Laid-Open No. 18533/78. In the case where $R^1$ represents an alkynyl group, for example, a propynyl group, the compound (I) may be converted into an α-methyl-4-biphenylylacetic acid which is a compound falling within the desired 4-biphenylylacetic acids by a method described in Japanese Patent Application Laid-Open No. 36642/77.

(2) Synthesis of the compound (II)

The compounds (II) may all be derived from a compound whose $R^2$ represents an alkylcarbonyl group.

For example, when cyclohexylbenzene is reacted with a carboxylic acid halide such as acetyl chloride by a Friedel-Crafts reaction, a 4-cyclohexylphenylalkyl (in this case, methyl) ketone ($R^2$=alkylcarbonyl) can be obtained.

If this ketone compound is nitrated, for example, a nitro group can be selectively introduced so as to produce a 4-cyclohexyl-3-nitrophenylalkyl ketone (X=nitro group). By subjecting this compound to a reduction reaction, a 3-amino-4-cyclohexylphenylalkyl ketone can be obtained. A halogen can be further introduced into the resultant ketone at its 3-position through a Sandmeyer reaction or a Schiemann reaction.

It is possible to convert the alkylcarbonyl group of the above mentioned ketone compound (in the formula (II), $R^2$=alkylcarbonyl group) into the other group within the definition of $R^2$. This conversion may be carried out by any method available for the conversion of the $R^1$ group of the above mentioned compound (I) or any other suitable method with due consideration of any influence on the subsequent dehydrogenation reaction. In the case where the group $R^2$ is dehydrogenatable, the dehydrogenation of the group $R^2$ can be carried out during the dehydrogenation of the compound (II).

(3) Synthesis of α-methyl-(2-fluoro-4-biphenylyl)-acetic acid

With regard to the preparation of α-alkyl (preferably, methyl)-(2-fluoro-4-biphenylyl)acetic acid which is most well known as an anti-inflammatory agent, one of the reactions for synthesizing the desired compound will be illustrated in detail hereunder by one embodiment of the present invention wherein cyclohexene and benzene are used as the starting material.

(1) Synthesis of cyclohexylbenzene

Cyclohexylbenzene can be synthesized by the Friedel-Crafts reaction of cyclohexane or cyclohexanol or cyclohexyl halide and benzene in the presence of a Lewis acid a typical example of which is anhydrous aluminum chloride. This reaction is ordinarily carried out in the presence of an excessive quantity of benzene at a temperature of from about −50° to 80° C., preferably from 0° to 40° C.

(2) Synthesis of 4-cyclohexylacetophenone

Cyclohexylacetophenone can be synthesized by reacting cyclohexylbenzene with acetyl chloride or acetic anhydride in the presence of a Lewis acid a typical example of which is anhydrous aluminum chloride. Illustrative of the solvents which can be used is carbon tetrachloride, carbon disulfide or nitrobenzene. However, any solvent which is inert to the reaction can be used. The reaction is carried out at a temperature of from −50° to 80° C., preferably from −20° to 25° C.

(3) Synthesis of 4-cyclohexyl-3-nitroacetophenone

Examples of the nitrating agent for 4-cyclohexylacetophenone are nitric acid, fuming nitric acid and acetyl nitrate. The use of a strong proton acid such as sulfuric acid as a catalyst promotes the nitration reaction. Examples of the solvent which can be used in the nitration reaction are sulfuric acid, acetic acid, acetic anhydride, dichloroethane and dioxane. However, any solvent which does not interfere with the nitration reaction can be used. The nitration reaction may be carried out at a temperature of from about −50° to 80° C., preferably from −30° to 25° C.

(4) Synthesis of 3-amino-4-cyclohexylacetophenone

The reductive amination of 4-cyclohexyl-3-nitroacetophenone can be carried out by catalytic hydrogenation with hydrogen or a chemical reduction using an acid and metals. The hydrogenation with hydrogen is ordinarily carried out in the presence of a catalyst. Any catalyst generally used for the reduction of a nitro group may be conveniently used. Examples of such a catalyst are Raney nickel, platinum oxide and palladium/carbon. The reduction reaction can be carried out with the hydrogen at atmospheric pressure, or at a pressure less than or greater than atmospheric pressure. It is preferable that the hydrogen pressure be in the range from about atmospheric pressure to 10 kg/cm². The solvent which can be used in the reduction reaction is any solvent which is stable under the reduction reaction and does not interfere with the reaction as well as solvents usually used for reduction reactions such as alcohols, ethers and aromatic hydrocarbons. The reaction temperature is in the range of from 0° to 120° C., preferably from 10° to 80° C.

The chemical reduction using an acid and a metal can be carried out by a process usually used for the reduction of a nitro group. Examples of the metal are a metal itself such as iron, tin and zinc or a metal salt such as stannous chloride and ferric chloride.

As the acid, hydrochloric acid, sulfuric acid or acetic acid is generally used. However, when ferric chloride is used as the metal, the use of an acid is not necessary because ferric chloride produces hydrochloric acid through its hydrolysis upon addition of water. As the solvent, use may be made of any solvent which is stable under the reaction and does not interfere with the reaction, such as alcohols, ethers, aromatic hydrocarbons, organic acids and their mixtures with water. The reaction temperature is in the range of from about 20° to 150° C., preferably from 40° to 120° C.

(5) Synthesis of 4-cyclohexyl-3-fluoroacetophenone

The conversion of 3-amino-4-cyclohexylacetophenone into 4-cyclohexyl-3-fluoroacetophenone can be carried out by a process known as a Schiemann reaction. More specifically, the Schiemann reaction comprises diazotizing 3-amino-4-cyclohexylacetophenone to the corresponding diazonium borofluoride salt, isolating the salt from the reaction mixture and thermally decomposing the salt.

Still more specifically, the diazonium borofluoride salt can be synthesized by reacting 3-amino-4-cyclohexylacetophenone with sodium nitrite or esters of nitrous acid in the presence of a borofluoride ion such as one derived from borofluoric acid. Alternatively, the diazonium borofluoride can be synthesized by diazotizing 3-amino-4-cyclohexylacetophenone with sodium nitrite or esters of nitrous acid in the presence of hydrochloric acid, sulfuric acid or nitric acid and, thereafter, adding a borofluoride ion such as borofluoric acid, sodium borofluoride and ammonium borofluoride to the reaction mixture. Lower alcohols, cyclic ethers or aqueous solutions thereof can be used as a solvent for these processes.

The reaction temperature is in the range from $-50°$ to 25° C., preferably from $-20°$ to 15° C., for the former process and in the range from $-50°$ to 15° C., preferably $-25°$ to 0° C., for the latter process. The subsequent thermal decomposition of the diazonium borofluoride salt is carried out at a temperature of from about 10° to 150° C., preferably from 20° to 60° C. The thermal decomposition is generally carried out in the absence of a solvent. However, it is preferable that it be carried out by dispersing the diazonium borofluoride salt into the medium of an organic solvent such as an aromatic or non-aromatic hydrocarbon, a cyclic or acyclic ether or halogenated hydrocarbon or an inorganic material such as barium sulfate and sand.

(6) Synthesis of 4-acetyl-2-fluorobiphenyl

This synthesis has been described in detail in the above given description of the dehydrogenation reaction.

(7) Synthesis of α-(2-fluoro-4-biphenylyl)ethyl alcohol

The synthesis of α-(2-fluoro-4-biphenylyl)ethyl alcohol by reduction of 4-acetyl-2-fluorobiphenyl can be carried out by both a catalytic hydrogenation with hydrogen or a chemical reduction by, for example, a metal hydride. The hydrogenation with hydrogen is generally carried out in the presence of a catalyst. As the catalyst, use can be made of any catalyst usually used for the reduction of a carbonyl group. Examples of such a catalyst are Raney nickel, copper chromite, platinum oxide and palladium/carbon. The hydrogen pressure is in the range from about atmospheric pressure to 300 $kg/cm^2$, preferably from atmospheric pressure to 150 $kg/cm^2$. The reaction temperature is in the range of from about room temperature to 200° C., preferably from room temperature to 120° C. The solvents which can be used in the reduction reaction are those which are usually used for reduction reactions, such as alcohols, cyclic or acyclic ethers and aromatic hydrocarbons provided that they are stable under the reaction and do not interfere with the reaction.

A representative chemical reduction process using a metal hydride is one which uses aluminum lithium hydride or sodium borohydride. The reaction condition depends upon the reagent used. For example, when aluminum lithium hydride is used, a cyclic or acyclic ether is generally used as a solvent. In some case, a solvent mixture of an ether and an aromatic hydrocarbon is used. The reduction temperature is in the range of from about $-20°$ to 100° C., preferably from 0° to 80° C.

In the case where the reducing reagent is sodium borohydride, a lower alcohol is usually used as a solvent. However, in some cases, a mixture of an alcohol with an ether or aromatic hydrocarbon is used. The temperature at which the reduction reaction is carried out is in the range of from about $-20°$ to 120° C., preferably from 0° to 60° C.

(8) Synthesis of 2-fluoro-4-vinylbiphenyl

A process for dehydrating α-(2-fluoro-4-biphenylyl)ethyl alcohol is described in detail in Japanese Pat. Laid-Open No. 18533/1978 directed to a prior invention by the present inventors.

Specifically, in accordance with one process, α-(2-fluoro-4-biphenylyl)ethyl alcohol is heated together with dimethyl sulfoxide at a temperature of from about 100° to 250° C., preferably from 130° to 190° C. Another process comprises passing α-(2-fluoro-4-biphenylyl)ethyl alcohol in vapor phase, which is diluted or not diluted with a diluent such as steam, or a volatile organic solvent such as an aromatic hydrocarbon and a cyclic ether or an inert gas such as nitrogen and carbon dioxide, over an alumina catalyst or a caustic alkali at a temperature of from about 150° to 450° C., preferably from 200° to 380° C.

(9) Synthesis of 2-(2-fluoro-4-biphenylyl)propionic acid

This synthesis is described in detail in the above cited Japanese Pat. Laid-Open No. 18533/1978.

More specifically, 2-fluoro-4-vinylbiphenyl is reacted with water and carbon monoxide in the presence of a palladium complex to form the desired 2-(2-fluoro-4-biphenylyl)propionic acid. The reaction is carried out at a carbon monoxide pressure of from about 20 to 800 $kg/cm^2$, preferably from 40 to 200 $kg/cm^2$ and at a temperature of from about 40° to 180° C., preferably from 50° to 150° C. In addition to a palladium complex which is used as a catalyst, a promotor comprising a mineral acid, such as hydrochloric acid, and/or a compound capable of being a ligand such as a phosphine and a nitrile may be added to the reaction system. Any solvent which is inert to the reaction and does not interfere with the reaction can be used. However, a liquid capable of dissolving the reactant and water together, such as dioxane and acetone, is preferable.

(4) General reaction system

Figure 1:
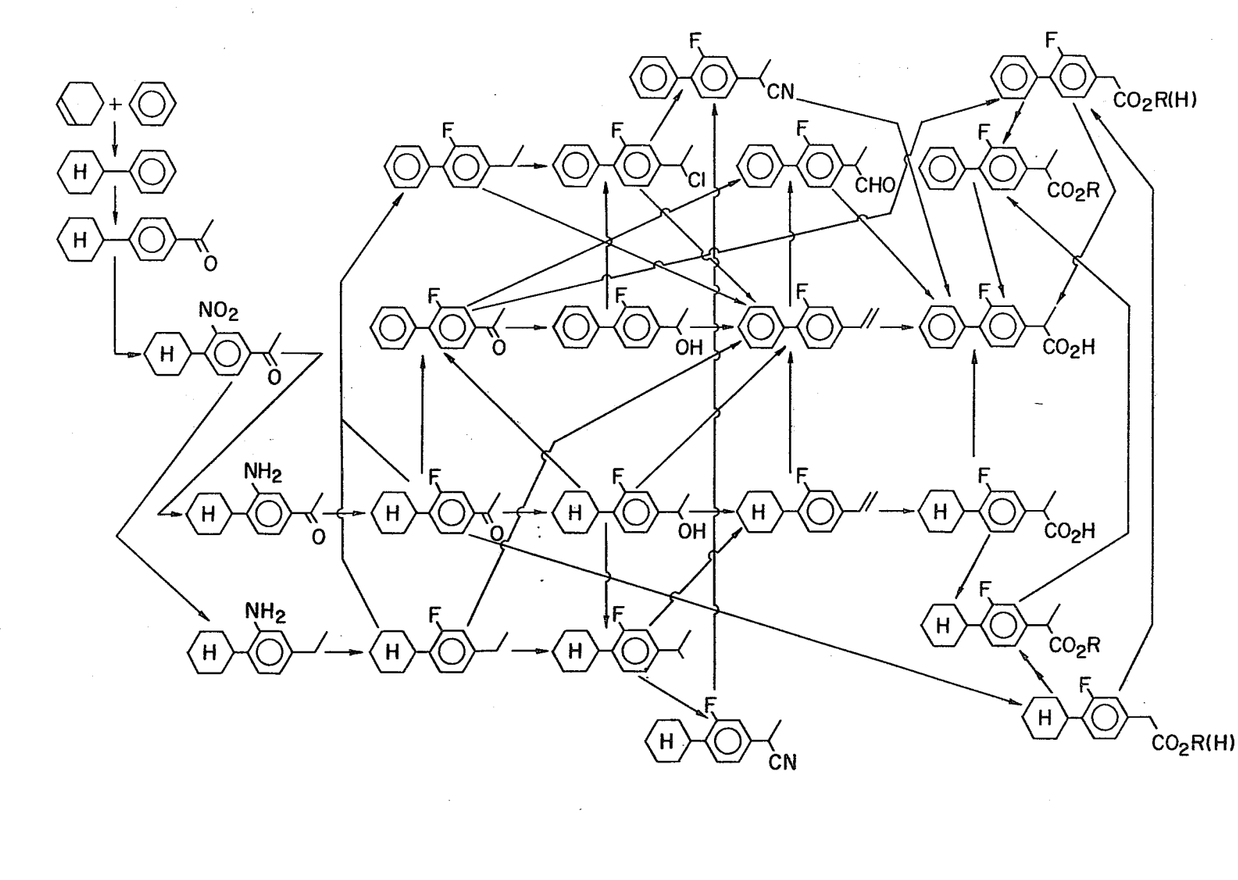

With regard to the production of α-alkyl (preferably methyl)-(2-fluoro-4-biphenylyl)acetic acid, a reaction system for synthesizing the desired compound by practicing one embodiment of the present invention wherein cyclohexane and benzene are used as the starting materials is shown in the accompanying drawing.

EXAMPLE 1

A mixture of 20 g of 4-cyclohexyl-3-fluoroacetophenone and 12 g of sulphur in 40 ml of diphenyl ether was subjected to heating with stirring at 260° C. for 10 hours. This step was followed by distillation of the reaction liquid. The resulting fraction obtained at 137° C. to 140.5° C. at 0.2 mmHg was recrystallized from n-hexane to produce 12.7 g of 4-acetyl-2-fluorobiphenyl (m.p. 97° to 97.5° C.).

EXAMPLE 2

A mixture of 5.00 g of α-methyl-4-cyclohexyl-3-fluorophenylacetic acid (m.p. 83° to 84° C.) and 2.3 g of sulphur in 10 ml of diphenyl ether was subjected to heating with stirring at 250° C. for 6 hours. The resulting reaction liquid was dissolved in acetone, and the insoluble substances were removed by filtration. The filtrate was poured into an aqueous sodium hydroxide solution. The resulting mixture was repeatedly washed with benzene, and hydrochloric acid was added to the aqueous layer. The crystals thus precipitated were collected by filtration, and recrystallized from a mixed benzene-n-hexane solvent to obtain 2.2 g of α-methyl-2-fluoro-4-biphenylylacetic acid (m.p. 112° to 114° C.).

EXAMPLE 3

A mixture of 6.93 g of α-methyl-4-cyclohexyl-3-fluorophenylacetonitrile ($n_D^{20}$ 1.5182) and 3.46 g of sulphur in 15 ml of diphenyl ether was subjected to heating with stirring at 250° C. for 4 hours. The resulting reaction liquid was diluted with acetone, and the insoluble substances therein were removed by filtration. The filtrate was concentrated and then distilled to obtain 5.06 g of α-methyl-(2-fluoro-4-biphenylyl)acetonitrile.

EXAMPLE 4

A mixture of 6.66 g of α-(4-cyclohexyl-3-fluorophenyl)ethyl alcohol and 3.46 g of sulphur in 15 ml of diphenyl ether was subjected to heating with stirring at 250° C. for 2 hours. The resulting reaction liquid was diluted with acetone, and insoluble substances were removed by filtration. The filtrate was subjected to the determination by gas chromatography (internal standard method). Thus, it was found that 3.51 g of 4-acetyl-2-fluorobiphenyl was obtained, and there remained 1.10 g of 4-cyclohexyl-3-fluoroacetophenone which was a reaction intermediate. The chemical structures were confirmed by gas chromatography-mass spectrum.

EXAMPLE 5

A solution of 569.1 g of titanium tetrachloride (TiCl₄) in 300 ml of ice water was poured into 3 N (normal) ammonia water with stirring to neutralize the mixture. The resulting precipitate was filtered and washed to obtain a cake. 567 g of the resulting cake (which was confirmed to contain 79.8 g of TiO₂ by the weight loss when baked at 800° C.) was taken, and a solution of 25.8 g of ammonium paratungstate [5(NH₄)₂O.12WO₃.5-H₂O] in 900 ml water was added thereto. The mixture was heated with sufficient stirring to evaporate off water until an extrudable paste was obtained. To the resulting paste was added 1 g of polyethylene oxide (tradename ALKOX E-30, supplied by Meisei Kagaku Kogyo, Japan). The resulting mixture was kneaded well and then extruded into a product of 5-mm diameter. The extruded product was dried and then baked at 800° C. for 2 hours. The resulting catalyst had a composition of Ti:W=9.1:0.9 in terms of metallic atom ratio.

The catalyst was ground to a fineness of 28 to 42 mesh, 20 ml of which was taken and used in the following reaction. As the reaction tube, a quartz tube having an inner diameter of 18 mm equipped therein with a quartz-protecting tube for thermocouple having a diameter of 4.5 mm was used. The reaction tube was heated in an electric oven, the temperature of wich was measured by thermocouples. The liquids supplied to the reaction tube comprise 0.3 m mol per hour of 4-cyclohexyl-3-fluoroacetophenone per 1 ml of the catalyst (hereinafter referred to as m mol/cc.hr), 0.7 m mol/cc.hr of toluene, and 11.2 m mol/cc.hr of water. The gas space velocity was therefore 273 hr⁻¹.

The products obtained at a reaction temperature of 590° C. were analysed by gas chromatography. The conversion of the starting material was 95.5%, and the selectivity with respect to the objective product 4-acetyl-2-fluorobiphenyl was 88.9%. Thus, the yield was 84.9%. Incidentally, the definitions of the conversion, selectivity, and yield are as follows.

$$\text{Conversion} = \frac{\left(\begin{array}{c}\text{quantity of}\\\text{starting mate-}\\\text{rial supplied}\end{array}\right) - \left(\begin{array}{c}\text{quantity of}\\\text{starting material}\\\text{not reacted}\end{array}\right)}{\left(\begin{array}{c}\text{quantity of starting mate-}\\\text{rial supplied}\end{array}\right)} \times 100$$

$$\text{Selectivity} = \frac{\left(\begin{array}{c}\text{quantity of objective product}\\\text{obtained}\end{array}\right)}{\left(\begin{array}{c}\text{quantity of}\\\text{starting mate-}\\\text{rial supplied}\end{array}\right) - \left(\begin{array}{c}\text{quantity of start-}\\\text{ing material not}\\\text{reacted}\end{array}\right)} \times 100$$

$$\text{Yield} = \frac{\left(\begin{array}{c}\text{quantity of objective}\\\text{product obtained}\end{array}\right)}{\left(\begin{array}{c}\text{quantity of starting}\\\text{material supplied}\end{array}\right)} \times 100$$

EXAMPLE 6

Titanium hydroxide was prepared in the same way as in Example 5, and zirconium oxide was prepared by dissolving 782 g of zirconyl chloride [ZrOCl₂.8H₂O] in water, neutralizing the solution with 3 N ammonia water, and then washing with water. The resulting 494 g of titanium hydroxide (containing 100 g of TiO₂) and 76.14 g zirconium oxide (17.14 g as ZrO₂) were mixed, and 1 g of the above-mentioned ALKOX E-30 was added thereto. The resulting mixture was amply kneaded and then extruded into a product 1 mm in diameter. The extruded product was dried and then baked at 800° C. for 2 hours. The resulting catalyst had a composition of Ti:Zr=9:1 in terms of metallic atom ratio.

The catalyst was ground to a fineness of 28 to 42 mesh, 20 ml of which was taken and used in the following reaction. 4-cyclohexyl-3-fluoroacetophenone, toluene, and water in a molar ratio of 0.05:0.95:1 were supplied to the reaction tube at a gas space velocity of 250 hr⁻¹. The reaction was carried out at 590° C. As a result, a conversion of 86.7% of the 4-cyclohexyl-3-fluoroacetophenone, a selectivity of 85.1% to 4-acetyl-2-fluorobiphenyl, and a yield of 73.8% was obtained.

EXAMPLE 7

The catalyst wherein Zr:W=9:1 was prepared in the same manner as in Example 6 by using zirconium hydroxide and ammonium paratungstate which had been obtained in the same way as in Example 6. Reaction was carried out by using the catalyst in the same way as in Example 6. As a result, a conversion of 97.6% of the 4-cyclohexyl-3-fluoroacetophenone, a selectivity of 85.9% to 4-acetyl-2-fluorobiphenyl, and a yield of 83.8% were obtained.

EXAMPLE 8

Iron nitrate was obtained by dissolving 360 g of iron powder in 4.05 kg of 51% (by weight) nitric acid. To the iron nitrate was added 15 l. of 3 N ammonia water to neutralize the mixture, and the resulting precipitate was washed with water. 430 g of the iron hydroxide thus obtained (100 g as $Fe_2O_3$) was taken and mixed with a solution of 36.3 g of ammonium paratungstate in 700 ml of water. A catalyst wherein Fe:W=9:1 was then obtained in the same way as in Example 6. Reaction was carried out in the same manner as in Example 6 by using the catalyst. As a result, a conversion of 94% of the 4-cyclohexyl-3-fluoroacetophenone, a selectivity of 85.7% to 4-acetyl-2-fluorobiphenyl, and a yield of 80.5% were obtained.

COMPARATIVE EXAMPLES 1 AND 2

Catalysts containing either titania or tungsten oxide were prepared in the same way as in Example 5. Reactions were carried out by using the catalysts under the conditions similar to those of Example 5, with the following results.

| | catalyst | reaction temperature (°C.) | 4-cyclohexyl-3-fluoroacetophenone conversion (%) | 4-acetyl-2-fluorobiphenyl selectivity (%) | yield (%) |
|---|---|---|---|---|---|
| Comparative Example 1 | $TiO_2$ | 620 | 42.7 | 57.6 | 24.6 |
| Comparative Example 2 | $WO_3$ | 590 | 45.3 | 76.6 | 34.7 |

COMPARATIVE EXAMPLE 3

Reaction was carried out by using Shell 105 catalyst (comprising $Fe_2O_3$—$Cr_2O_3$—$K_2O$), which is generally employed as a catalyst for dehydrogenation of ethylbenzene, in the same manner as in Example 5. Most of the products were defluorinated compounds.

COMPARATIVE EXAMPLE 4

Reaction was carried out by using a catalyst (supplied by Nippon Engelhard Company, Japan) wherein 5% of palladium was supported on activated carbon, in the same manner as in Example 5. Defluorinated products were mostly obtained.

EXAMPLE 9

α-(4-cyclohexyl-3-fluoro)phenylethyl alcohol was employed as the starting material. The same $TiO_2$—$WO_3$ catalyst as that employed in Example 5 was used. Reaction was carried out at a gas space velocity of 420 hr$^{-1}$ in the same manner as in Example 6. As a result, a conversion of 100% of the starting material, a yield of 26% of 4-ethyl-2-fluorobiphenyl, a yield of 27% of 4-vinyl-2-fluorobiphenyl, and a yield of 31% of 4-acetyl-2-fluorobiphenyl were obtained.

EXAMPLE 10

The process of Example 5 was repeated except that 4-cyclohexyl-3-fluoroethylbenzene was used as the starting material, and a gas space velocity of 250 hr$^{-1}$ was used. As a result, a conversion of 100% of the starting material, a yield of 41% of 4-ethyl-2-fluorobiphenyl, and a yield of 42% of 4-vinyl-2-fluorobiphenyl were obtained.

EXAMPLE 11

A commercially available γ-alumina (1.6 mm cylindrical form, supplied by Ketjen Company under the tradename of CK-300) was ground into fine powder. A solution of 113.7 g of ammonium paratungstate in 2 liter water was added to 200 g of the fine powder thus obtained. The mixture was heated with ample stirring to evaporate off water. A small amount of water was added to the resulting powder, which was then subjected to wet grinding in a grinding mill (Ishikawa agitation mill). The resulting paste was extruded into a product 1 mm in diameter, which was dried and then baked in a muffle furnace at 800° C. for 2 hours. The catalyst thus obtained had a composition of Al:W=9:1 in terms of metallic atom ratio.

In the following reaction, 20 ml of the catalyst which had been ground to a fineness of 28 to 42 mesh, was used and the starting material gas having the same composition as in Example 6 was employed at a gas space velocity of 260 hr$^{-1}$. The reaction was carried out at a temperature of 560° C. As a result, a conversion of 98.9% of the 4-cyclohexyl-3-fluoroacetophenone, a selectivity of 84.2% to 4-acetyl-2-fluorobiphenyl, and a yield of 83.3% were obtained.

EXAMPLE 12

A solution of 500 g of cerous nitrate [Ce(NO$_3$)$_3$.n-H$_2$O] in 2 liter water was adjusted to a pH with 3 N ammonia water to obtain a precipitate. The precipitate was collected by filtration and evaporated to dryness on a water bath. The resulting powder was baked in a muffle furnace at 350° C. for 3 hours to decompose the remaining nitrate. Then, 204 g of the powder thus obtained (200 g as CeO$_2$) was taken, and a solution of 33.7 g of ammonium paratungstate in 800 ml water was added thereto. The mixture was heated with ample stirring and evaporated to dryness. The resulting powder together with a small amount of water was subjected to wet grinding in a grinding mill. The paste thus obtained was extruded into a product 1 mm in diameter, which was dried and then baked at 800° C. for 2 hours. The resulting catalyst had a composition of Ce:W=9:1 in terms of metallic atom ratio. The catalyst was ground to a fineness of 28 to 42 mesh, 20 ml of which was taken and used in the following reaction. Reaction was carried out under the conditions set forth in Example 6 except that the reaction temperature was 620° C. As a result, a conversion of 96.3% of the 4-cyclohexyl-3-fluoroacetophenone, a selectivity of 80.9% to 4-acetyl-2-fluorobiphenyl, and a yield of 78.0% were obtained.

EXAMPLE 13

To 200 g (1.96 mol as Al) of the powder obtained by grinding a commercially available γ-Al$_2$O$_3$ (supplied by Ketjen Company under the tradename of CK-300), was added 119.3 g (0.218 mol) of hydrated zirconium oxide [ZrO$_2$.xH$_2$O], after which 500 ml water was further added. The mixture was evaporated with ample stirring to dryness. The resulting powder was subjected to wet grinding together with a small amount of water in a grinding mill. The paste thus obtained was extruded into a product 1 mm in diameter, which was then dried and baked at 800° C. for 2 hours.

The resulting catalyst had a composition of Al:Zr=9:1 in terms of metallic atom ratio. The catalyst was ground to a fineness of 28 to 42 mesh, 20 ml of which was taken and used in the following reaction. Reaction was carried out at a reaction temperature of 560° C. in the same way as in Example 6. As a result, a conversion of 97.3% of the 4-cyclohexyl-3-fluoroacetophenone, a selectivity of 69.9% of 4-acetyl-2-fluorobiphenyl, and a yield of 68.1% were obtained.

What is claimed is:

1. A process for producing a halobiphenyl derivative represented by a formula (I) which comprises dehydrogenating a cyclohexylhalobenzene represented by a formula (II) in the presence of a dehydrogenating agent selected from the group consisting of (1) a catalyst selected from the group consisting of tungsten oxide, zirconium oxide and mixtures thereof as an active component supported on a refractory inorganic support and (2) sulfur under such conditions that no substantial dehalogenation occurs,
the formula (I) being (I)

the formula (II) being (II)

wherein X represents a halogen atom, and $R^1$ and $R^2$ independently represent a group represented by the formula wherein A represents a carboxyl or alkoxycarbonyl group and R represents a hydrogen atom or lower alkyl group; an alkylcarbonyl; alkenyl; alkyl; hydroxyalkyl or cyanoalkyl.

2. A process as claimed in claim 1, wherein the dehydrogenation comprises heating said compound (II) at a temperature of from 200° to 350° C. in the presence of at least a theoretical quantity of sulfur.

3. A process as claimed in clam 2, wherein the heating is carried out in a liquid dispersion medium.

4. A process as claimed in claim 1, wherein the dehydrogenation comprises catalyst dehydrogenation which is carried out over a catalyst consisting essentially of a catalytically active component supported on a refractory inorganic compound, which component is selected from the group consisting of a tungsten oxide, a zirconium oxide, and mixtures of a tungsten oxide and a zirconium oxide at a temperature of from 300° to 800° C.

5. A process as claimed in claim 4, wherein the refractory support is an oxide consisting essentially of at least one member selected from the group consisting of titanium, zirconium, aluminum, iron, calcium, magnesium, cerium, and tin.

6. A process as claimed in claim 4, wherein the refractory support is an oxide comprising, at least one member selected from the group consisting of titanium, zirconium, aluminum, iron and cerium.

7. A process as claimed in any one of claims 1 to 6, wherein $R^1$ and $R^2$ are acetyl, respectively, and X is fluorine.

8. A process according to claim 1 in which said dehydrogenation is carried out by reacting said cycloheylhalobenzene with a least a theroretical amount of sulfur at about 200° to 350° C. in a liquid medium or by contacting said cyclohexylhalobenzene at about 300° to 800° C. with a catalyst supported on a refractory inorganic compound, wherein said catalyst is selected from the group consisting of an oxide of tungsten, zirconium or a combination thereof and said refractory support is selected from a member of the group consisting of an oxide of titanium, zirconium, aluminum, iron, calcium, magnesium, cerium and tin, with the proviso that zirconium oxide is not the refractory support when zirconsium is the catalyst.

* * * * *

UNITED STATES PATENT AND TRADEMARK OFFICE
CERTIFICATE OF CORRECTION

PATENT NO. : 4,263,457
DATED : April 21, 1981
INVENTOR(S) : TAKEDA ET AL.

It is certified that error appears in the above-identified patent and that said Letters Patent are hereby corrected as shown below:

1. A process for producing a halobiphenyl derivative represented by a formula (I) which comprises dehydrogenerating a cyclohexylhalobenzene represented by a formula (II) in the presence of a dehydrogenating agent selected from the group consisting of (1) a catalyst consisting essentially of a catalytically active component supported on a refractory inorganic support, said catalytically active component being selected from the group consisting of tungsten oxide, zirconium oxide and mixtures thereof and (2) sulfur under such conditions that no substantial dehalogenation occurs, the formula (I) being the formula (II) being wherein X represents a halogen atom, and $R^1$ and $R^2$ independently represent a group represented by the formula wherein A represents a carboxyl or alkoxycarbonyl group and R represents a hydrogen atom or lower alkyl group; an alkylcarbonyl; alkenyl; alkyl; hydroxyalkyl or cyanoalkyl group.

continued........

UNITED STATES PATENT AND TRADEMARK OFFICE
CERTIFICATE OF CORRECTION

PATENT NO. : 4,263,457
DATED : April 21, 1981
INVENTOR(S) : TAKEDA ET AL.

It is certified that error appears in the above-identified patent and that said Letters Patent are hereby corrected as shown below:

4. A process as claimed in claim 1, wherein the dehydrogenation comprises catalytic dehydrogenation which is carried out over a catalyst consistting essentially of a catalytically active component supported on a refractory inorganic compound, which component is selected from the group consisting of a tungsten oxide, a zirconium oxide, and mixtures of a tungsten oxide and a zirconium oxide at a temperature of from 300° to 800° C.

8. A process according to claim 1, in which said dehydrogenation is carried out by reacting said cyclohexylhalobenzene with at least a theoretical amount of sulfur at about 200° to 350°C. in a liquid medium or by contacting said cyclohexylhalobenzene at about 300° to 800°C. with a catalyst supported on a refractory inorganic compound, wherein said catalyst is selected from the group consisting of an oxide of tungsten, zirconium or a combination thereof and said refractory support is selected from a member of the group consisting of an oxide of titanium, zirconium, aluminum, iron, calcium, magnesium, cerium and tin, with the proviso that zirconium oxide is not the refractory support when zirconium is the catalyst.

Signed and Sealed this

Thirty-first Day of August 1982

[SEAL]

Attest:

GERALD J. MOSSINGHOFF

Attesting Officer   Commissioner of Patents and Trademarks